United States Patent [19]

Sundeen et al.

[11] 4,382,081

[45] * May 3, 1983

[54] INHIBITORS OF MAMMALIAN COLLAGENASE

[75] Inventors: Joseph E. Sundeen, Yardley, Pa.; Tamara Dejneka, Skillman, N.J.

[73] Assignee: E. R. Squibb & Sons, Inc., Princeton, N.J.

[*] Notice: The portion of the term of this patent subsequent to Nov. 25, 1997, has been disclaimed.

[21] Appl. No.: 273,142

[22] Filed: Jun. 12, 1981

[51] Int. Cl.³ .................... A61K 37/00; C07C 103/52
[52] U.S. Cl. .............................. 424/177; 260/112.5 R
[58] Field of Search ................ 424/177; 260/112.5 R

[56] References Cited

U.S. PATENT DOCUMENTS 4,235,885 11/1980 Sundeen et al.

FOREIGN PATENT DOCUMENTS 1989 6/1979 European Pat. Off.

OTHER PUBLICATIONS

"Structure-Inhibition Relationships Among Metal-binding Collagen Peptide Analogues", Hossain Saneii* and Arno F. Spatola* (SPON: John W. Brown), University of Louisville, Louisville, KY 40292, May 1, 1981, vol. 40, No. 6.

*Primary Examiner*—Delbert R. Phillips
*Attorney, Agent, or Firm*—Lawrence S. Levinson; Burton Rodney

[57] ABSTRACT

Mammalian collagenase is inhibited by compounds of the formula

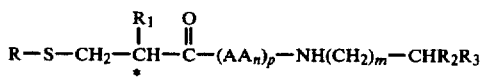

or salts thereof, wherein R is hydrogen, alkanoyl of 2 to 10 carbon atoms or arylcarbonyl;

$R_1$ is of 3 to 8 carbon atoms, cycloalkyl of 3 to 7 carbon atoms, aryl or arylalkyl;

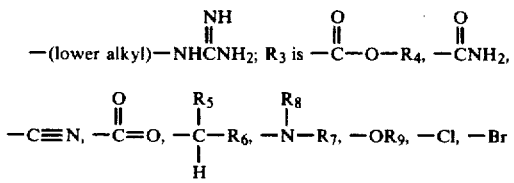

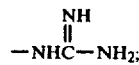

$R_4$ is hydrogen, methyl, ethyl, or

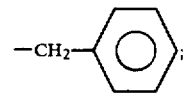

$R_5$ and $R_6$ are each independently selected as $-OCH_3$ or $-OCH_2CH_3$ or are combined as $-OCH_2CH_2O-$ or $-O-(CH_2)-O-$;

$R_7$ and $R_8$ are each independently selected as hydrogen, methyl or ethyl or are combined as $-(CH_2)_4-$, $-(CH_2)_5-$ or $-CH_2CH_2-O-CH_2CH_2-$;

$R_9$ is hydrogen, methyl, ethyl

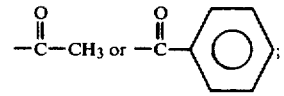

m is an integer from 0 to 7; p is an integer from 1 to 3;

$AA_n$ is an amino acid chain of from one to three amino acids; n is 1 or 1, 2 or 1, 2, 3;

when p is 1, $AA_n$ is $AA_1$;
when p is 2, $AA_n$ is $AA_1-AA_2$;
when p is 3, $AA_n$ is $AA_1-AA_2-AA_3$;

$AA_1$ is glycine or alanine;
$AA_2$ is glycine or alanine;
$AA_3$ is leucine, glutamine or isoleucine.

A method of reducing the adverse effects of mammalian collagenase in a mammalian host in need thereof, which comprises administering to the mammal an effective amount of a compound having the above formula is within the scope of the invention.

10 Claims, No Drawings

INHIBITORS OF MAMMALIAN COLLAGENASE

RELATED APPLICATIONS

U.S. patent application Ser. No. 154,748 filed May 30, 1980 discloses mammalian collagenase inhibitors having the formula

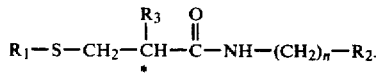

wherein
- $R_1$ is hydrogen, alkanoyl of 2 to 10 carbon atoms or arylcarbonyl;
- $R_2$ is 1-pyrrolidinyl, 1-piperidinyl, 4-morpholinyl, 1-piperazinyl, or 4-alkyl-1-piperazinyl;
- $R_3$ is alkyl of 3 to 8 carbon atoms, cycloalkyl of 3 to 7 carbon atoms, aryl, or arylalkyl; and
- n is an integer of 1 to 20.

BACKGROUND OF THE INVENTION

European Patent Application Ser. No. 1,989, published May 30, 1979, discloses compounds having the formula

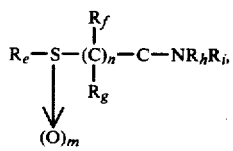

wherein the symbols are, inter alia, as follows: $R_e$ is hydrogen, m is 0, $R_f$ and $R_g$ are hydrogen, alkyl, cycloalkyl, arylalkyl, or aryl, $R_h$ and $R_i$ are hydrogen, aminoalkyl, alkylaminoalkyl, dialkylaminoalkyl, phenylaminoalkyl, diphenylaminoalkyl, (phenyl) (alkyl)aminoalkyl, or heterocyclic and n is 1 to 17. The compounds are disclosed as useful for the treatment of diseases characterized or complicated by an imbalance of immune hemostasis. The treatment of rheumatoid arthritis is specifically disclosed.

Sundeen, et al. in U.S. Pat. No. 4,235,885 issued Nov. 25, 1980 disclose mammalian collagenase inhibitors having the formula

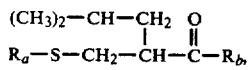

wherein $R_a$ is hydrogen or alkanoyl of 2 to 10 carbon atoms; $R_b$ is hydroxy, amino or

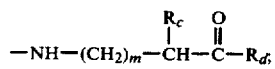

$R_c$ is hydrogen, alkyl of 1 to 4 carbon atoms,

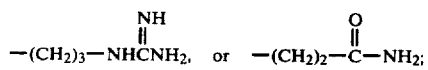

$R_d$ is hydroxy, amino, arginine, leucine, glutamine, alanine or glycine; and m is 0 or an integer of 1 to 9.

SUMMARY OF THE INVENTION

Mammalian collagenase is inhibited by compounds of the formula

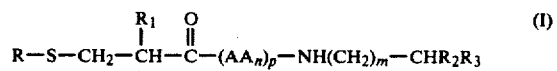

or salts thereof. In formula I and throughout this specification the symbols are as defined below. R is hydrogen, alkanoyl of 2 to 10 carbon atoms (acetyl is preferred) or arylcarbonyl (benzoyl is preferred);

$R_1$ is alkyl of 3 to 8 carbon atoms, cycloalkyl of 3 to 7 carbon atoms, aryl or arylalkyl;

$R_2$ is hydrogen, $$-\text{lower alkyl-}\overset{\overset{O}{\|}}{C}NH_2 \text{ (ethyl is preferred) or}$$

$$-\text{lower alkyl-}NH\overset{\overset{NH}{\|}}{C}NH_2 \text{ (propyl is preferred);}$$

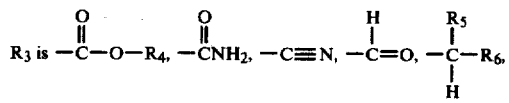

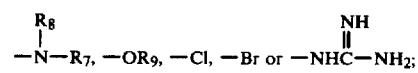

$R_4$ is hydrogen, lower alkyl (methyl and ethyl are preferred), or arylalkyl (preferrably phenylmethylene)

$R_5$ and $R_6$ are each independently selected as $-OCH_3$ or $-OCH_2CH_3$ or are combined as $-OCH_2-CH_2O-$ or $-O-(CH_2)_3-O-$;

$R_7$ and $R_8$ are each independently selected as hydrogen, lower alkyl, (methyl and ethyl are preferred) or are combined as $-(CH_2)_4-$, $-(CH_2)_5-$ or $-CH_2CH_2-O-CH_2CH_2-$ $R_9$ is hydrogen, lower alkyl (methyl and ethyl are preferred),

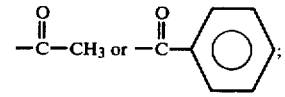

m is an integer from 0 to 7; p is an integer from 1 to 3. $AA_n$ is an amino acid chain of from one to three amino acids; n is 1 or 1, 2 or 1, 2, 3; when p is 1, $AA_n$ is $AA_1$; when p is 2, $AA_n$ is $AA_1$-$AA_2$; when p is 3, $AA_n$ is $AA_1$-$AA_2$-$AA_3$;

$AA_1$ is glycine or alanine;
$AA_2$ is glycine or alanine;
$AA_3$ is leucine, glutamine or isoleucine.

The term "aryl", as used throughout the specification, either individually or as part of a larger group, refers to phenyl or phenyl substituted with one, two or three alkyl, alkoxy, halogen, amino, hydroxy, or alkanoyloxy groups. Phenyl and monosubstituted phenyl are the preferred aryl groups.

The terms "alkyl," "alkanoyl," "alkoxy," and "lower alkyl," as used throughout the specification (unless otherwise defined), either individually or as part of a larger group, refer to groups having 1 to 8 carbon atoms.

The term halogen, as used throughout the specification, either individually or as part of a larger group, refers to fluorine, chlorine, bromine and iodine.

DETAILED DESCRIPTION OF THE INVENTION

The compounds of formula I have at least one asymmetric carbon atom; the carbon noted with an asterisk (*) in formula I. The compounds accordingly exist in stereomeric forms or as racemic mixtures thereof. All of these are within the scope of this invention. The above described synthesis can utilize the starting compounds in the form of a racemic mixture or as a stereomer.

The compounds of formula I can be made by treating a compound of the formula $$R-S-CH_2-\overset{R_1}{\underset{*}{CH}}-\overset{O}{\overset{\|}{C}}-OH \quad (II)$$

wherein R is alkanoyl or arylcarbonyl in a solvent such as tetrahydrofuran with a coupling agent such as dicyclohexylcarbodiimide and N-hydroxysuccinimide and treating the resulting mixture with an $AA_1$ amino acid i.e. alanine or glycine to obtain a compound of the formula $$R-S-CH_2-\overset{R_1}{\underset{*}{CH}}-\overset{O}{\overset{\|}{C}}-AA_1. \quad (III)$$

To obtain formula I compounds wherein p is 1 the compound of formula III in a solvent such as tetrahydrofuran is treated with a coupling agent such as dicyclohexylcarbodiimide and N-hydroxysuccinimide and the resulting mixture is then treated with a compound of formula $$NH_2-(CH_2)_m-\underset{H}{\overset{R_2}{\underset{|}{C}}}-R_3 \quad (IV)$$

to obtain a compound of formula I.

By treatment of the resulting formula I compound wherein R is alkanoyl or arylcarbonyl with ammonium hydroxide the corresponding formula I compound is obtained wherein R is hydrogen.

To obtain formula I compounds wherein p is 2, a compound of formula III in a solvent such as tetrahydrofuran is treated with a coupling agent such as dicyclohexylcarbodiimide and N-hydroxysuccinimide and the resulting mixture is treated with an $AA_2$ amino acid i.e. alanine or glycine to obtain a compound of the formula $$R-S-CH_2-\overset{R_1}{\underset{*}{CH}}-\overset{O}{\overset{\|}{C}}-AA_1-AA_2. \quad (V)$$

The compound of formula V in a solvent such as tetrahydrofuran is treated with a coupling agent such as dicyclohexylcarbodiimide and N-hydroxysuccinimide and the resulting mixture is then treated with a compound of formula IV to obtain a compound of formula I.

To obtain a formula I compound wherein p is 3 a compound of formula III in a solvent such as tetrahydrofuran is treated with a coupling agent such as dicyclohexylcarbodiimide and N-hydroxysuccinimide and the resulting mixture is treated with an $AA_3$ amino acid i.e. leucine, glutamine or isoleucine to obtain a compound of the formula $$R-S-CH_2-\overset{R_1}{\underset{*}{CH}}-\overset{O}{\overset{\|}{C}}-AA_1-AA_2-AA_3. \quad (VI)$$

The compound of formula VI in a solvent such as tetrahydrofuran is treated with a coupling agent such as dicyclohexylcarbodiimide and p-nitrophenol and the resulting mixture is then treated with a compound of formula IV to obtain a compound of formula I.

Compounds of formula II are obtained by treating a compound of formula $$H_5C_2-O-\overset{O}{\overset{\|}{C}}-\overset{R_1}{\underset{|}{CH}}-\overset{O}{\overset{\|}{C}}-OC_2H_5 \quad (VII)$$

with sodium hydroxide to obtain a compound of the formula $$HO-\overset{O}{\overset{\|}{C}}-\overset{R_1}{\underset{|}{CH}}-\overset{O}{\overset{\|}{C}}-OH. \quad (VIII)$$

The compound of formula VIII is then treated with dimethyl amine and formaldehyde to obtain a compound of formula $$HO-\overset{O}{\overset{\|}{C}}-\underset{\underset{CH_2-N\overset{CH_3}{\underset{CH_3}{\diagdown}}}{\overset{R_1}{\underset{|}{C}}}}{}-\overset{O}{\overset{\|}{C}}-OH \quad (IX)$$

Treating the compound of formula IX with sodium hydroxide and heating, a compound of formula X is obtained $$H_2C=\overset{R_1}{\underset{|}{C}}-\overset{O}{\overset{\|}{C}}-OH \quad (X)$$

A compound of formula II is obtained by treating the formula X compound with a compound of the formula $$R-SH. \quad (XI)$$

Compounds of formula VII are obtained by treating diethylmalonate with ethanol and sodium ethoxide mixture, and then treated with a compound of the formula $$R_1-Br \quad (XII)$$

to form a compound of formula VII.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

The compounds of formula I wherein $R_2$ is H and $R_3$ is $NR_7R_8$ form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have at least one asymmetric carbon atom; the carbon noted with an asterisk (*) in formula I. The compounds accordingly exist in stereomeric forms or in racemic mixtures thereof. All of these are within the scope of this invention. The above described synthesis can utilize the starting compounds in the form of a racemic mixture or as a stereomer. L-isomers with respect to the carbon atoms of the amino acids is generally preferred.

In mammals, collagenase is one of the key enzymes involved in the cartilage and joint destruction of rheumatoid arthritis; see, for example, *Arthritis and Rheumatism*, 20 (6):1231 (1977). It is, therefore, desirable to inhibit the action of the collagenase enzyme.

While not limiting the scope of this invention to a specific theory or mechanism of operation, it is nevertheless helpful to an understanding of the invention to review the possible reasons for the activity of the compounds of formula I. The main components of cartilage are the collagen polypeptide molecules. These polypeptides are cleaved by mammalian collagenase at a single site. The compounds of this invention resemble the susceptible sequence of the collagen molecules and, it is theorized, bind to the mammalian collagenase enzyme and inhibit its activity.

Tha mammalian collagenase enzyme contains zinc, which assists in the cleavage of a glycine-leucine or glycine-isoleucine bond and contains an extended cleft which interacts with an extended portion of the collagen molecule. This molecule in turn contains arginine as the last homologous amino acid in the substrate sequence adjacent to the cleavage site, a sequence showing a high degree of homology among the various types of collagen molecules. The inhibitors of this invention make use of these features of the enzyme and make modifications to enhance binding to the mammalian collagenase molecule.

The action of mammalian collagenase has also been implicated as a causative factor of disease in several other mammals. These diseases include periodontal disease, corneal ulceration, tumor invasiveness, and epidermolysis bullosa; see, for example, *American Journal of Pathology*, 92 (2):509 (1978) and *The New England Journal of Medicine*, 291 (13):652 (1974).

For use in the treatment of rheumatoid arthritis, the compounds of this invention can be administered to a mammal in need thereof either orally or by injection intraarticularly into the affected joint. The daily dosage for a 70 kilogram mammal will be in the range of about 10 milligrams to 1 gram.

The compounds of this invention can be formulated in compositions such as tablets, capsules or elixirs for oral administration or in sterile solutions or suspentions for parenteral administration. About 10 to 500 mg of a compound of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are specific embodiments of this invention.

EXAMPLE 1

N-[N-[[N-[2-(Mercaptomethyl)-4-methyl-1-oxopentyl]-L-alanyl]glycyl]-L-leucyl]-L-arginine, isomer A (a) Isobutyldiethyl malonate Diethyl malonate is treated with an ethanol and sodium ethoxide mixture. Then iso-butyl bromide is added to form isobutyl diethyl malonate as the product of this malonic ester synthesis.

(b) 2-(S-Acetylthiomethyl)4-methylpentanoic acid

Hydrolysis of 91.1 g of isobutyldiethyl malonate is accomplished by digesting a solution of the ester in 300 ml of methanol and 400 ml of 10% NaOH for 6 hours at 80° C. The solution is concentrated in vacuo to 400 ml. It is acidified with 10% aqueous HCl and product is extracted with ethyl acetate to yield 67.6 g of the diacid. This crystallized on standing. M.P. 94°-95° C.

The diacid is suspended in 400 ml of water and cooled to 5° C. Aqueous 40% dimethylamine (50 g) and aqueous 37% formaldehyde (35.7 g) are added in that order. The solution is stirred overnight and Mannich base solid product is filtered and dried in vacuo to yield 57.3 g. M.P. 134°-137° C. with $CO_2$ and dimethylamine given off.

The Mannich base (57.3 g) is suspended in 200 ml of water and 43 g of 50% NaOH in 100 ml of water is added until pH is 9. This solution is heated on the steam cone under nitrogen overnight. It is neutralized with 10% HCl and product is extracted with ethyl acetate to yield 23.8 g. The crude unsaturated acid is chromatographed (twice) on 200 g of silica to give 21.6 g of pure acid.

This unsaturated pure acid (4.3 g) is stirred with 5 ml of thiolacetic acid overnight. It is then concentrated in vacuo until crystallization occurs. Yield 3.6 g of 2-(S-acetylthiomethyl)4-methylpentanoic acid M.P. 42°-47° C.

(c) (±)-N-[2-(S-Acetylmercaptomethyl)-4-methyl-1-oxopentyl]-L-alanine 2-(S-acetylthiomethyl)4-methylpentanoic acid (2.04 g, 0.1 mole) is dissolved in 20 ml of dry dioxane. The solution is cooled to 15° C. and N-hydroxysuccinimide (1.15 g, 0.1 mole) is added followed by the portionwise addition of dicyclohexylcarbodiimide. This is stirred at room temperature for 5 hours and then is filtered into a 15 ml aqueous solution of $NaHCO_3$ (0.84 g) and alanine (0.90 g). After stirring for 20 hours the reaction mixture is concentrated in vacuo. The pot residue is dissolved in water (20 ml) and washed with ethyl acetate. The aqueous solution is acidified with conc. HCl and product is extracted with ethyl acetate. Ethyl acetate is dried with MgSO$_4$, filtered and concentrated in vacuo to yield 1.5 g of crude product. This is placed on 50 g of silica and 250 ml of petroleum ether is filtered through followed by 250 ml of 1:1 ether-petroleum ether. Product is eluted with 250 ml of ether to yield 1.2 g. This is further purified by preparing the dicyclohexylamine salt in isopropyl ether. M.P. 157°–167° C. Analysis is consistent for product containing 1.5 mole of water.

Analysis calc'd. for C$_{24}$H$_{44}$N$_2$O$_3$S.1.5 H$_2$O: C, 61.63; H, 10.13; N, 5.99; S, 6.85. Found: C, 61.69; H, 9.88; N, 6.03; S, 7.01.

The free acid is liberated by dissolving the salt in 10% aqueous KHSO$_4$ and extracting with ethyl acetate. This is dried with MgSO$_4$, filtered and concentrated in vacuo to yield (±)-N-[2-(S-acetylmercaptomethyl)-4-methyl-1-oxopentyl]-L-alanine. Analysis is consistent for product containing ⅔ mole of water.

Analysis calc'd. for C$_{12}$H$_{21}$NO$_4$S.⅔ H$_2$O: C, 49.89; H, 7.85; N, 4.85; S, 11.10. Found: C, 49.87; H, 7.74; N, 4.69; S, 11.39.

(d) N-[N-[[N-[2-(Mercaptomethyl)-4-methyl-1-oxopentyl]L-alanyl]-glycyl]-L-leucyl]-L-arginine, isomer A:

The above free acid, (±)-N-[2-(S-acetylmercaptomethyl)-4-methyl-1-oxopentyl]-L-alanine (1.6 g) is dissolved in 60 ml of dioxane. This is cooled to 15° C. and N-hydroxysuccinimide (0.67 g) is added followed by the portionwise addition of (1.2 g) dicyclohexylcarbodiimide (DCC). This is stirred at 20° C. for 5 hours, then filtered into a 4 ml aqueous solution (0.44 g) of glycine and (0.49 g) NaHCO$_3$. After stirring at room temperature for 20 hours, the reaction mixture is concentrated in vacuo. The residue is dissolved in 14 ml of water and is washed with ethyl acetate. The aqueous solution is acidified with 10% HCl to pH 2 and product is extracted with ethyl acetate. The ethyl acetate is dried with MgSO$_4$, filtered and concentrated in vacuo. Purification is carried out by preparing the dicyclohexyl amine salt in ethyl acetate at pH 8. Formation of gelatinous solid is slow. After 2 hours solution is filtered to give a solid, m.p. 138°–148° C. This is reconverted to the free acid by dissolving in water, neutralizing with 10% aqueous KHSO$_4$ and extracting product with ethyl acetate. Ethyl acetate is dried with MgSO$_4$, filtered and concentrated in vacuo to yield 1.4 g of product. Yield 72%.

The above product (1.4 g) is dissolved in 30 ml of dioxane and cooled to 15° C. N-Hydroxysuccinimide (0.49 g) is added, followed by the portionwise addition (0.87 g) of DCC. The reaction mixture is stirred at ambient temperature for 5 hours. It is then filtered into a 30 ml aqueous solution of L leucine and (0.35 g) NaHCO$_3$. After stirring at room temperature overnight the reaction mixture is concentrated in vacuo. The pot residue is dissolved in 100 ml of water and this solution is washed with ethyl acetate. The aqueous solution is cooled to 5° C. and neutralized with 10% HCl. The aqueous solution is saturated with NaCl and product is extracted with ethyl acetate. Ethyl acetate is dried with MgSO$_4$, filtered, and concentrated in vacuo to yield 2.0 g of clear, colorless oil. This is washed with pentane then with ether. Addition of ether caused crystallization. Solid is filtered and dried at 60° C. in vacuo. Yield: 1.0 g. M.P. 135°–141° C. [α]$_D^{20°\ C.}$ = −36° 1% solution in 95% ethanol.

Anal. Calc'd. for C$_{20}$H$_{35}$N$_3$O$_6$S.⅓ H$_2$O: C, 52.84; H, 7.98; N, 9.24; S, 7.05. Found: C, 52.99; H, 7.91; N, 9.30; S, 7.09.

The above product (0.44 g) is dissolved in 25 ml of ethyl acetate and cooled to 5° C. To this is added (0.14 g) p-nitrophenol followed by the portionwise addition of (0.20 g) dicyclohexylcarbodiimide. This is stirred at 0° C. overnight. The reaction mixture is filtered and the filtrate is concentrated in vacuo. After washing with hexane the residue is dissolved in a minimal amount of ethyl acetate. A second crop of dicyclohexylurea is filtered off and the filtrate yields 0.7 g of crude active ester as a viscous yellow oil. This is dissolved in 30 ml of tetrahydrofuran (THF) and cooled to 5° C. Arginine (0.16 g) in 30 ml of water is added dropwise to the tetrahydrofuran solution. The reaction mixture is stirred at 5° C. for four hours, then at room temperature overnight. It is concentrated in vacuo and dissolved in 30 ml of water. This is washed with portions of ethyl acetate until the aqueous solution is almost colorless. It is then lyophilized to about 5 ml and chromatographed through 70 g of Avicel (cellulose) using 1:4 H$_2$O:C-H$_3$OH. After 250 ml of solvent passes through column, product is eluted in 100 ml to yield 0.4 g of N-[N-[[N-[2-(mercaptomethyl)-4-methyl-1-oxopentyl]-L-alanyl]-glycyl]-L-leucyl]-L-arginine, isomer A as product.

Anal. Calc'd. for C$_{26}$H$_{47}$N$_7$O$_7$S.1.4H$_2$O: C, 49.81; H, 8.01; N, 15.64; S, 5.11.

Found: C, 50.03; H, 7.89; N, 15.33; S, 5.10.

The above product (0.35 g) is dissolved in 20 ml of argon purged water and cooled to 5° C. Concentrated NH$_4$OH (1 ml) is added and the reaction mixture is stirred at room temperature for 2 hours. The reaction mixture is lyophilized to dryness. Product is washed thoroughly with acetonitrile and dried in vacuo overnight at 40° C. M.P. begins to soften at 150° C.–160° C. [α]$_D^{20°\ C.}$ = −15.5° in 95% ethanol.

Anal. Calc'd for C$_{24}$H$_{45}$N$_7$O$_6$S.0.9H$_2$O: C, 50.05; H, 8.19; N, 17.02; S, 5.57. Found: C, 50.38; H, 8.25; N, 16.61; S, 5.49.

EXAMPLES 2–20

By following the procedure of Example 1 but substituting a compound of Column I for isobutyldiethyl malonate, using a compound of Column II in place of thiol acetic acid, substituting a compound of Column III in place of alanine, deleting the steps adding glycine and leucine, substituting a compound of Column IV in place of arginine and deleting final treatment with ammonium hydroxide, a compound of Column V is formed.

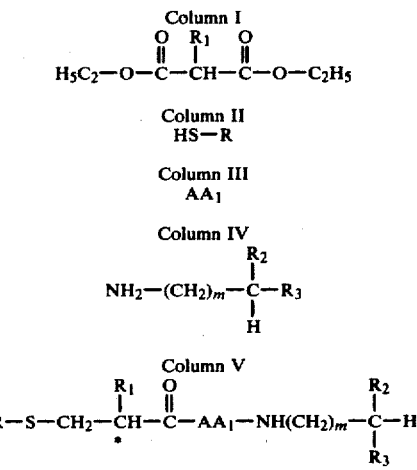

| Example | R | $R_1$ | $R_2$ | $R_3$ | $R_4$ | $R_5$ | $R_6$ | $R_7$ | $R_8$ | $R_9$ | m | p | $AA_1$ |
|---|---|---|---|---|---|---|---|---|---|---|---|---|---|
| 2 | $\underset{\|}{O}=\overset{\|}{C}-CH_3$ | $-CH_2-CH(CH_3)_2$ | $-H$ | $-C\equiv N$ | — | — | — | — | — | — | 1 | 1 | glycine |
| 3 | $O=C-$ phenyl | $\begin{array}{c}CH_3\\\|\\-CH\\\|\\CH_2-CH_3\end{array}$ | $-(CH_2)_2-\underset{\|}{\overset{O}{C}}-NH_2$ | $\underset{\|}{\overset{O}{C}}-H$ | — | — | — | — | — | — | 0 | 1 | alanine |
| 4 | $O=C-$ phenyl | $-CH_2-$ phenyl | $-(CH_2)_3-NH-\underset{\|}{\overset{NH}{C}}-NH_2$ | $\underset{\|}{\overset{R_5}{C}}-R_6$ | — | $-O-(CH_2)_3-O-$ | — | — | — | — | 2 | 1 | alanine |
| 5 | $O=C-$ phenyl | $-CH_2-$ phenyl | $-H$ | $\underset{\|}{N}\overset{R_7}{\underset{R_8}{\diagdown}}$ | — | — | — | $-H$ | $-H$ | — | 3 | 1 | alanine |
| 6 | $O=C-$ phenyl | $-CH_2-$ phenyl | $-H$ | $-O-R_9$ | — | — | — | — | — | $-H$ | 4 | 1 | alanine |
| 7 | $O=C-$ phenyl | $-CH_2-$ phenyl | $-H$ | $-Cl$ | — | — | — | — | — | — | 5 | 1 | alanine |
| 8 | $O=C-$ phenyl | $-CH_2-$ phenyl | $-H$ | $-Br$ | — | — | — | — | — | — | 6 | 1 | alanine |
| 9 | $O=C-$ phenyl | $-CH_2-$ phenyl | $-H$ | $-NH-\underset{\|}{\overset{NH}{C}}-NH_2$ | $-CH_3$ | — | — | — | — | — | 7 | 1 | alanine |
| 10 | $O=C-$ phenyl | $-CH_2-$ phenyl | $-H$ | $\underset{\|}{\overset{O}{C}}-OR_4$ | — | — | — | — | — | — | 2 | 1 | alanine |
| 11 | $O=C-$ phenyl | $-CH_2-$ phenyl | $-H$ | $\underset{\|}{\overset{O}{C}}-NH_2$ | — | — | — | — | — | — | 2 | 1 | alanine |

-continued

| Example | R | R₁ | R₂ | R₃ | R₄ | R₅ | R₆ | R₇ | R₈ | R₉ | m | p | AA₁ |
|---|---|---|---|---|---|---|---|---|---|---|---|---|---|
| 12 | $O=\overset{\|}{C}-C_2H_5$ | $-CH(CH_2-CH_2)_2CH-$ (cyclohexyl) | —H | $O=\overset{\|}{C}-OR_4$ | —H | — | — | — | — | — | 1 | 1 | glycine |
| 13 | $O=\overset{\|}{C}-CH_3$ | $-CH(CH_3)_2$ | —H | $O=\overset{\|}{C}-OR_4$ | —C₂H₅ | — | — | — | — | — | 3 | 1 | glycine |
| 14 | $O=\overset{\|}{C}-CH_3$ | —CH₂—(phenyl) | —H | $O=\overset{\|}{C}-OR_4$ | —CH₂—(phenyl) | — | — | — | — | — | 4 | 1 | glycine |
| 15 | $O=\overset{\|}{C}-CH_3$ | —CH₂—(phenyl) | —H | $\overset{R_5}{\underset{R_6}{>}}CH-$ | — | —O—(CH₂)₂—O— | | — | — | — | 1 | 1 | glycine |
| 16 | $O=\overset{\|}{C}-CH_3$ | —CH₂—(phenyl) | —H | $\overset{R_5}{\underset{R_6}{>}}CH-$ | — | —OCH₃ | —OCH₃ | — | — | — | 1 | 1 | glycine |
| 17 | $O=\overset{\|}{C}-CH_3$ | —CH₂—(phenyl) | —H | $\overset{R_7}{\underset{R_8}{>}}N-$ | — | — | — | —(CH₂)₂—O—(CH₂)₂— | | — | 1 | 1 | glycine |
| 18 | $O=\overset{\|}{C}-CH_3$ | —CH₂—(phenyl) | —H | —OR₉ | — | — | — | — | — | —CH₃ | 1 | 1 | glycine |
| 19 | $O=\overset{\|}{C}-CH_3$ | —CH₂—(phenyl) | —H | —OR₉ | — | — | — | — | — | $O=\overset{\|}{C}-$(phenyl) | 1 | 1 | glycine |
| 20 | $O=\overset{\|}{C}-CH_3$ | —CH₂—(phenyl) | —H | —OR₉ | — | — | — | — | — | $O=\overset{\|}{C}-CH_3$ | 1 | 1 | glycine |

EXAMPLES 21–39

By following the procedure of Example 1 but substituting a compound of Column I for isobutyldiethyl malonate, using a compound of Column II in place of thiol acetic acid, substituting a compound of Column III in place of alanine, substituting a compound of Column IV in place of glycine deleting the step of adding leucine, substituting a compound of Column V in place of arginine and deleting final treatment with ammonium hydroxide, a compound of Column VI is formed.

Column I

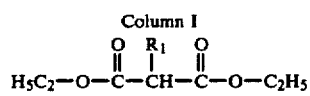

Column II

-continued
HS—R

Column III
$AA_1$

Column IV
$AA_2$

Column V

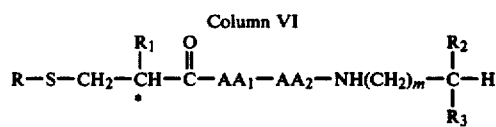

Column VI

R—S—CH$_2$—CH(R$_1$)—C(O)—AA$_1$—AA$_2$—NH(CH$_2$)$_m$—C(R$_2$)(R$_3$)—H

| Example | R | $R_1$ | $R_2$ | $R_3$ | $R_4$ | $R_5$ | $R_6$ | $R_7$ | $R_8$ | $R_9$ | m | p | $AA_1$ | $AA_2$ |
|---|---|---|---|---|---|---|---|---|---|---|---|---|---|---|
| 21 | $\overset{O}{\underset{\|}{-C}}-CH_3$ | $-CH_2-CH(CH_3)_2$ | $-H$ | $-C{\equiv}N$ | — | — | — | — | — | — | 1 | 2 | glycine | glycine |
| 22 | $\overset{O}{\underset{\|}{-C}}-\text{Ph}$ | $\underset{CH_2-CH_3}{\overset{CH_3}{-CH}}$ | $-(CH_2)_2-\overset{O}{\underset{\|}{C}}-NH_2$ | $\overset{O}{\underset{\|}{=C}}-H$ | — | — | — | — | — | — | 0 | 2 | alanine | alanine |
| 23 | $\overset{O}{\underset{\|}{-C}}-\text{Ph}$ | $-CH_2-\text{Ph}$ | $-(CH_2)_3-NH-\overset{NH}{\underset{\|}{C}}-NH_2$ | $\underset{H}{\overset{R_5}{-C-R_6}}$ | — | $-O-(CH_2)_5-O-$ | | — | — | — | 2 | 2 | alanine | glycine |
| 24 | $\overset{O}{\underset{\|}{-C}}-\text{Ph}$ | $-CH_2-\text{Ph}$ | $-H$ | $\underset{R_8}{\overset{R_7}{N}}$ | — | — | — | $-H$ | $-H$ | — | 3 | 2 | alanine | glycine |
| 25 | $\overset{O}{\underset{\|}{-C}}-\text{Ph}$ | $-CH_2-\text{Ph}$ | $-H$ | $-O-R_9$ | — | — | — | — | — | $-H$ | 4 | 2 | alanine | glycine |
| 26 | $\overset{O}{\underset{\|}{-C}}-\text{Ph}$ | $-CH_2-\text{Ph}$ | $-H$ | $-Cl$ | — | — | — | — | — | — | 5 | 2 | alanine | glycine |
| 27 | $\overset{O}{\underset{\|}{-C}}-\text{Ph}$ | $-CH_2-\text{Ph}$ | $-H$ | $-Br$ | — | — | — | — | — | — | 6 | 2 | alanine | glycine |
| 28 | $\overset{O}{\underset{\|}{-C}}-\text{Ph}$ | $-CH_2-\text{Ph}$ | $-H$ | $-NH-\overset{NH}{\underset{\|}{C}}-NH_2$ | — | — | — | — | — | — | 7 | 2 | alanine | glycine |
| 29 | $\overset{O}{\underset{\|}{-C}}-\text{Ph}$ | $-CH_2-\text{Ph}$ | $-H$ | $\overset{O}{\underset{\|}{=C}}-OR_4$ | $-CH_3$ | — | — | — | — | — | 2 | 2 | alanine | glycine |
| 30 | $\overset{O}{\underset{\|}{-C}}-\text{Ph}$ | $-CH_2-\text{Ph}$ | $-H$ | $\overset{O}{\underset{\|}{=C}}-NH_2$ | — | — | — | — | — | — | 2 | 2 | alanine | glycine |

-continued

| Example | R | R₁ | R₂ | R₃ | R₄ | R₅ | R₆ | R₇ | R₈ | R₉ | m | p | AA₁ | AA₂ |
|---|---|---|---|---|---|---|---|---|---|---|---|---|---|---|
| 31 | −C(=O)−C₂H₅ | −CH₂−CH₂−CH(CH₂−CH₂)− (cyclohexyl) | −H | −C(=O)−OR₄ | −H | — | — | — | — | — | 1 | 2 | glycine | glycine |
| 32 | −C(=O)−CH₃ | −CH(CH₃)CH₃ | −H | −C(=O)−OR₄ | −C₂H₅ | — | — | — | — | — | 3 | 2 | glycine | alanine |
| 33 | −C(=O)−CH₃ | −CH₂−C₆H₅ | −H | −C(=O)−OR₄ | −CH₂−C₆H₅ | — | — | — | — | — | 4 | 2 | glycine | alanine |
| 34 | −C(=O)−CH₃ | −CH₂−C₆H₅ | −H | −CH(R₅)(R₆) | — | −O−(CH₂)₂−O | | — | — | — | 1 | 2 | glycine | alanine |
| 35 | −C(=O)−CH₃ | −CH₂−C₆H₅ | −H | −N(R₇)(R₈) | — | −OCH₃ | −OCH₃ | — | — | — | 1 | 2 | glycine | alanine |
| 36 | −C(=O)−CH₃ | −CH₂−C₆H₅ | −H | −N(R₇)(R₈) | — | — | — | −(CH₂)₂−O−(CH₂)₂− | | — | 1 | 2 | glycine | alanine |
| 37 | −C(−O)−CH₃ | −CH₂−C₆H₅ | −H | −OR₉ | — | — | — | — | — | −CH₃ | 1 | 2 | glycine | alanine |
| 38 | −C(−O)−CH₃ | −CH₂−C₆H₅ | −H | −OR₉ | — | — | — | — | — | −C(=O)−C₆H₅ | 1 | 2 | glycine | alanine |
| 39 | −C(−O)−CH₃ | −CH₂−C₆H₅ | −H | −OR₉ | — | — | — | — | — | −C(=O)−CH₃ | 1 | 2 | glycine | alanine |

EXAMPLES 40-58

By following the procedure of Example 1 but substituting a compound of Column I for isobutyldiethyl malonate, using a compound of Column II in place of thiol acetic acid, substituting a compound of Column III in place of alanine, substituting a compound of Column IV in place of glycine, using a compound of Column V in place of leucine, substituting a compound of Column VI in place of arginine and deleting final treatment with ammonium hydroxide, a compound of Column VII is formed.

Column I

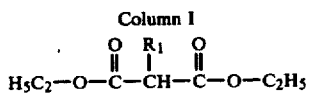

Column II

HS—R

Column III
AA$_1$

Column IV
AA$_2$

Column V
AA$_3$

Column VI

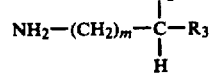

Column VII

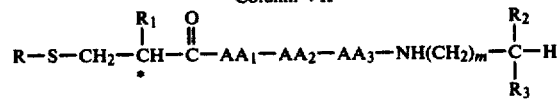

| Example | R | $R_1$ | $R_2$ | $R_3$ | $R_4$ | $R_5$ | $R_6$ | $R_7$ | $R_8$ | $R_9$ | m | p | $AA_1$ | $AA_2$ | $AA_3$ |
|---|---|---|---|---|---|---|---|---|---|---|---|---|---|---|---|
| 40 | $-\overset{O}{\underset{\|}{C}}-CH_3$ | $-CH_2-CH(CH_3)_2$ | $-H$ | $-C\equiv N$ | — | — | — | — | — | — | 1 | 3 | glycine | alanine | leucine |
| 41 | $-\overset{O}{\underset{\|}{C}}-\phi$ | $\overset{CH_3}{\underset{\|}{-CH}}-CH_2-CH_3$ | $-(CH_2)_2-\overset{O}{\underset{\|}{C}}-NH_2$ | $-\overset{O}{\underset{\|}{C}}-H$ | — | — | — | — | — | — | 0 | 3 | alanine | alanine | leucine |
| 42 | $-\overset{O}{\underset{\|}{C}}-\phi$ | $-CH_2-\phi$ | $-(CH_2)_3-NH-\overset{NH}{\underset{\|}{C}}-NH_2$ | $-\overset{R_5}{\underset{R_6}{\overset{\|}{C}-}}-H$ | — | $-O-(CH_2)_3-O-$ | | — | — | — | 2 | 3 | alanine | alanine | leucine |
| 43 | $-\overset{O}{\underset{\|}{C}}-\phi$ | $-CH_2-\phi$ | $-H$ | $-\overset{R_7}{\underset{R_8}{N}}$ | — | — | — | $-H$ | $-H$ | — | 3 | 3 | alanine | alanine | glutamine |
| 44 | $-\overset{O}{\underset{\|}{C}}-\phi$ | $-CH_2-\phi$ | $-H$ | $-O-R_9$ | — | — | — | — | — | $-H$ | 4 | 3 | alanine | alanine | glutamine |
| 45 | $-\overset{O}{\underset{\|}{C}}-\phi$ | $-CH_2-\phi$ | $-H$ | $-Cl$ | — | — | — | — | — | — | 5 | 3 | alanine | alanine | glutamine |
| 46 | $-\overset{O}{\underset{\|}{C}}-\phi$ | $-CH_2-\phi$ | $-H$ | $-Br$ | — | — | — | — | — | — | 6 | 3 | alanine | alanine | glutamine |
| 47 | $-\overset{O}{\underset{\|}{C}}-\phi$ | $-CH_2-\phi$ | $-H$ | $-NH-\overset{NH}{\underset{\|}{C}}-NH_2$ | — | — | — | — | — | — | 7 | 3 | alanine | alanine | glutamine |
| 48 | $-\overset{O}{\underset{\|}{C}}-\phi$ | $-CH_2-\phi$ | $-H$ | $-\overset{O}{\underset{\|}{C}}-OR_4$ | $-CH_3$ | — | — | — | — | — | 2 | 3 | alanine | glycine | isoleucine |
| 49 | $-\overset{O}{\underset{\|}{C}}-\phi$ | $-CH_2-\phi$ | $-H$ | $-\overset{O}{\underset{\|}{C}}-NH_2$ | — | — | — | — | — | — | 2 | 3 | alanine | glycine | isoleucine |

-continued

| Example | R | R₁ | R₂ | R₃ | R₄ | R₅ | R₆ | R₇ | R₈ | R₉ | m | p | AA₁ | AA₂ | AA₃ |
|---|---|---|---|---|---|---|---|---|---|---|---|---|---|---|---|
| 50 | $\overset{O}{\underset{\|}{-C}}-C_2H_5$ | $-CH\begin{smallmatrix}CH_2-CH_2\\ \\CH_2-CH_2\end{smallmatrix}CH_2$ | —H | $\overset{O}{\underset{\|}{-C}}-OR_4$ | —H | — | — | — | — | — | 1 | 3 | glycine | glycine | isoleucine |
| 51 | $\overset{O}{\underset{\|}{-C}}-CH_3$ | $-CH\begin{smallmatrix}CH_3\\ \\CH_3\end{smallmatrix}$ | —H | $\overset{O}{\underset{\|}{-C}}-OR_4$ | —C₂H₅ | — | — | — | — | — | 3 | 3 | glycine | glycine | leucine |
| 52 | $\overset{O}{\underset{\|}{-C}}-CH_3$ | —CH₂—⌬ | —H | $\overset{O}{\underset{\|}{-C}}-OR_4$ | —CH₂—⌬ | — | — | — | — | — | 4 | 3 | glycine | glycine | leucine |
| 53 | $\overset{O}{\underset{\|}{-C}}-CH_3$ | —CH₂—⌬ | —H | $-CH\begin{smallmatrix}R_5\\ \\R_6\end{smallmatrix}$ | — | —O—(CH₂)₂—O— | | — | — | — | 1 | 3 | glycine | alanine | leucine |
| 54 | $\overset{O}{\underset{\|}{-C}}-CH_3$ | —CH₂—⌬ | —H | $-CH\begin{smallmatrix}R_5\\ \\R_6\end{smallmatrix}$ | — | —OCH₃ | —OCH₃ | — | — | — | 1 | 3 | glycine | alanine | leucine |
| 55 | $\overset{O}{\underset{\|}{-C}}-CH_3$ | —CH₂—⌬ | —H | $-N\begin{smallmatrix}R_7\\ \\R_8\end{smallmatrix}$ | — | — | — | —CH₃ | —C₂H₅ | — | 1 | 3 | glycine | alanine | leucine |
| 56 | $\overset{O}{\underset{\|}{-C}}-CH_3$ | —CH₂—⌬ | —H | —OR₉ | — | — | — | — | — | —CH₃ | 1 | 3 | glycine | alanine | leucine |
| 57 | $\overset{O}{\underset{\|}{-C}}-CH_3$ | —CH₂—⌬ | —H | —OR₉ | — | — | — | — | — | $\overset{O}{\underset{\|}{-C}}-⌬$ | 1 | 3 | glycine | alanine | leucine |
| 58 | $\overset{O}{\underset{\|}{-C}}-CH_3$ | —CH₂—⌬ | —H | —OR₉ | — | — | — | — | — | $\overset{O}{\underset{\|}{-C}}-CH_3$ | 1 | 3 | glycine | alanine | leucine |

EXAMPLE 59

(±)-N-[2-(Dimethylamino)ethyl]-N-$^2$-[2-(mercaptomethyl)-4-methyl-1-oxopentyl]glycinamide, barbituric acid (1:1) salt A. (±)-N-[2-(Acetylmercaptomethyl)-4-methyl-1-oxopentyl]glycine A solution of 860 ml (3.74 mole) of 25% of NaOCH$_3$ in CH$_3$OH and an equal volume of CH$_3$OH is warmed to near reflux. Dimethyl malonate (425 ml, 3.74 mole) is added, followed by 410 ml (3.74 mole) of 1-bromo-2-methyl propane. Heating back to reflux gives a clear yellow solution. Refluxing under N$_2$ for 18 hours gives a slurry. While at reflux a total of 425 ml of 50% NaOH is added plus enough water to dissolve the precipitated salts, for a total reaction volume of 5 liters. The basic (pH=14) mixture is refluxed until little cloudiness is observed on dilution of a sample with water. Distillation until T≅90°, cooling in ice, acidification with 25% H$_2$SO$_4$ to pH=1, and extraction with 4 liters of ethyl acetate gives on drying and evaporation, a slurry. Benzene is added and the slurry evaporated to a solid. Trituration with hexane, filtering and drying in air gives 402 g, m.p. 101°-105° (67%). An additional 25 g, m.p. 92°-101°, were obtained on further extraction with ethyl acetate and rework of the mother liquors, for a total of 427 g (71%). A 410 g (2.56 mole) sample of isobutyl malonic acid is dissolved in 3.5 liters of water. This yellow solution is cooled in ice and treated with 288 g (2.56 mole) of 40% aqueous dimethylamine. Stirring with cooling is continued, and when the internal temperature equals 10° C., 210 g (2.56 mole) of 37% formalin is added. The resulting clear yellow solution is stored at 5° C. for 2½ days, whereupon it is a solid mass of white solid. This mixture is carefully brought to near reflux (foaming) with stirring, and held there until the solution is clear and CO$_2$ is no longer evolved to a significant extent (heated 2 hours after complete solution). The mixture is cooled in ice and acidified strongly with 350 ml of 7.2 M H$_2$SO$_4$ (pH=1). Extraction with 2 liters of hexane and drying (Na$_2$SO$_4$) gives 206 g of isobutyl acrylic acid. Extraction with another 2 liters of hexane gives 6 g, for a total of 212 g (65%) of the unsaturated acid.

A 206 g (1.61 mole) sample of isobutyl acrylic acid and 175 ml of thionyl chloride are reacted by simultaneous slow addition to a heated (∼60° C.) flask, with venting to a NaOH trap. After the addition is complete and SO$_2$ evolution has subsided (2 hours of heating), the mixture is cooled and the house vacuum applied. Slow warming achieves the distillation of excess SOCl$_2$ (dry ice trap), as judged by the ir of the residue. The residue is the acid chloride, 218 g (93%), and is used without further purification.

A solution of 218 g (1.49 mole) of isobutyl acryloyl chloride in an equal volume of methylene chloride is added to a mixture of 212 g (1.52 mole) of ethyl glycinate hydrochloride and 308 g (3.06 mole) of triethylamine in 3.5 liters of CH$_2$Cl$_2$ at T=10°-12° C. (ice cooling) over ¾ hour. The mixture is stirred at room temperature for 2½ days, then extracted once with dilute H$_2$SO$_4$, dilute NaHCO$_3$, dried (Na$_2$SO$_4$), and evaporated to give 323 g of solid ester (318 g theory), m.p. 55°-60° C.

The ester is slurried in 800 ml of CH$_3$OH and treated with a solution of 120 g of 50% NaOH in <100 ml of water. Warming spontaneously and for 10 minutes on a steam cone gives a solution with pH=9. Another 300 ml of 10% NaOH is added, and, after 15 minutes, the mixture is acidified to pH=1 with 6 N H$_2$SO$_4$. Extraction with 5 liters ethylacetate, drying (Na$_2$SO$_4$), and evaporation gives an oil. Benzene (600 ml) is added and evaporated, finally under good vacuum, to give 274 g (99%) of solid, m.p. 73°-81°.

The above acid (274 g, 1.48 mole) is dissolved in 3 liters of chloroform and treated with 125 ml of "Evans" thiolacetic acid. By NMR, 50% of the unsaturation will have gone by 3 hours and 75% in 18 hours. Another 50 ml of thiolacetic acid is added, and in another 24 hours, a white solid precipitates. Filtering and washing with CHCl$_3$ and drying in air give 224 g (58%), (±)-N-[2-(acetylmercaptomethyl)-4-methyl-1-oxopentyl]glycine, m.p. 120°-121°.

A sample of the filtrates shows 10% unsaturated by NMR, so 50 ml more thiolacetic acid is added for 2½ days. Distillation down to 1.5 liters and dilution with hexane gives 76 g, m.p. 108°-120°, for a total yield of 300 g, 78%.

B. (±)-N$^2$-[2-[(Acetylthio)methyl]-4-methyl-1-oxopentyl]-N-[2-(dimethylamino)ethyl]glycinamide, barbituric acid (1:1) salt A 2.61 g (0.01 mole) sample of (±)-N-[2-(acetylmercaptomethyl)-4-methyl-1-oxopentyl]glycine is slurried in 50 ml of CH$_2$Cl$_2$. Triethylamine (1.08 g, 0.01 mole) is added to give a solution which is cooled to −10° C. and treated with 1.08 g (0.01 mole) of ethyl chloroformate. After ½ hour, a solution of N,N-dimethylethylenediamine (0.88 g, 0.01 mole) in 10 ml of CH$_2$Cl$_2$ is added, and stirring from −5° C. to +25° C. continued for 2 hours. The mixture is evaporated and triturated with ethyl acetate. The triethylamine hydrochloride is filtered and the filtrates evaporated to an oil, 3.6 g. A 2.95 g sample of oil is dissolved with 1 equivalent of barbituric acid in methanol, filtered and evaporated to a foam. Addition of acetonitrile gives a white solid which is washed (briefly) with absolute ethanol and then acetonitrile. Recrystallization from 100 ml of acetonitrile gives a white powder, 1.3 g of (±)-N$^2$-[2-[(acetylthio)methyl]-4-methyl-1-oxopentyl]-N-[2-(dimethylamino)ethyl]glycinamide, barbituric acid (1:1) salt (34%), m.p. 151°-154°, which analyzes correctly for a salt with 1.0 mole of barbituric acid and 0.5 mole of water.

Anal. Calc'd for C$_{15}$H$_{29}$N$_3$O$_3$S.C$_4$H$_4$N$_2$O$_3$.0.5 H$_2$O: C, 48.70, H, 7.31; N, 14.95; S, 6.84. Found: C, 48.74, H, 7.05; N, 15.13; S, 6.88.

C. (±)-N-[2-(Dimethylamino)ethyl-N$^2$-[2-(mercaptomethyl)-4-methyl-1-oxopentyl]glycinamide, barbituric acid (1:1) salt An 0.5 g sample of pure (±)-N$^2$-[2-[(acetylthio)methyl]-4-methyl-1-oxopentyl]-N-[2-(dimethylamino)ethyl]glycinamide, barbituric acid (1:1) salt in 10 ml of water at 0° C. under argon is treated with 2 ml of concentrated NH$_4$OH and allowed to rise to 25° over 2 hours to give a slurry of white solid. This mixture is evaporated in vacuo, water added and lyophilized. Trituration with CH$_3$CN gives a solid which is filtered and dried in vacuo. Absolute ethanol is added, the slurry filtered and the filtrates diluted with ether to give a solid, m.p. 125°-135°, which after drying at 25° over P$_2$O$_5$ in vacuo analyzes as the monobarbiturate monohydrate, 0.2 g of (±)-N-[2-(dimethylamino)ethyl]-N$^2$-[2-(mercaptomethyl)-4-methyl-1-oxopentyl]glycinamide, barbituric acid (1:1) salt (40%).

Anal. Calc'd for C$_{13}$H$_{27}$N$_3$O$_2$S.C$_4$H$_4$N$_2$O$_3$.1.0 H$_2$O: C, 46.87; H, 7.64; N, 16.08; S, 7.30. Found: C, 46.80; H, 7.29; N, 16.43; S, 7.15.

EXAMPLE 60

(±)-N-[4-[(Aminoiminomethyl)amino]butyl]-N$^2$-[2-(mercaptomethyl)-4-methyl-1-oxopentyl]glycinamide, acetate (1:1) salt A. (±)-N$^2$-[2-(Acetylthio)methyl]-[4-methyl-1-oxopentyl]-N-[4-[(aminoiminomethyl)amino]butyl]-glycinamide, acetate (1:1) salt Agmatine sulfate (1.40 g) is dissolved in 10 ml of water. To this is added two equivalents (1.01 g) of sodium acetate. This solution is concentrated in vacuo and the residue is slurried with hot ethanol and filtered. The filtrate is concentrated in vacuo and washed with ethyl acetate. Yield 1.5 g, m.p. 132°–136° C., NMR consistent for agmatine mono acetate.

The p-nitrophenyl ester of N-(2-(S-acetylmercapto methyl)-4-methyl-1-oxopentyl glycine prepared as described in U.S. Pat. No. 4,235,885 (2.7 g, 0.007 mole) is dissolved in THF and cooled to 5° C. The above agmatine acetate (0.8 g, 0.005 mole) is dissolved in 10 ml of water and this solution is added dropwise to the active ester. It is slurried overnight and concentrated in vacuo to 10 ml. This aqueous solution is diluted to 20 ml with water and is washed with ethyl acetate until the aqueous solution is colorless. It is lyophilized overnight to yield 2.2 g of material which after washing with acetonitrile gives 1.5 g of analytical product. M.P. softens at 58° C. NMR consistent.

B. (±)-N-[4-[(Aminoiminomethyl)amino]butyl]-N$^2$-[2-(mercaptomethyl)-4-methyl-1-oxopentyl]glycinamide, acetate (1:1) salt (±)-N$^2$-[2-[(Acetylthio)methyl]-4-methyl-1-oxopentyl]-N-[4-[(aminoiminomethyl)amino]butyl]glycinamide, acetate (1:1) salt (0.9 g) is dissolved in 10 ml of water, and purged with argon. To this is added 2 ml of concentrated NH$_4$OH. After stirring at room temperature for 2 hours, the reaction mixture is lyophilized almost to dryness. Acetic acid (5 ml) is added and concentrated again in vacuo. The glassy material is washed two times with acetonitrile to separate out acetamide. Ammonium acetate, the other by product, is separated out by drying the product at 100° C. in vacuo for two hours. Analytical product is a low melting glassy solid (0.4 g).

EXAMPLE 61

(±)-4-[[[[-2-(Mercaptomethyl)-4-methyl-1-oxopentyl]amino]acetyl]amino]butanoic acid A. (±)-4-[[[[2-[(Acetylthio)methyl]-4-methyl-1-oxopentyl]amino]acetyl]amino]butanoic acid, N-cyclohexylcyclohexanamine salt (1:1)

A solution of N-[2-[(acetylthio)methyl]-4-methyl-1-oxopentyl]glycine, p-nitrophenyl ester prepared as described in U.S. Pat. No. 4,235,885 (1.9 g, 5 mmoles) in 50 ml of THF at 0° C. is treated with a solution of 4-aminobutyric acid (0.58 g, 5.5 mmoles) and sodium bicarbonate (0.42 g, 5 mmoles) in 10 ml of water. Stirring overnight at 0°–25° C. is followed by stripping to an aqueous solution, extracting (EtOAc) until colorless, and acidifying the aqueous with KHSO$_4$. Extraction (EtOAc) gives an oil which is purified by flash filtration on 60–200 mesh silica gel in EtOAc and EtOAc/MeOH. The purified acid is converted to the dicyclohexylamine salt in EtOAc, and the solvent removed in vacuo. The residue is washed with ether, then covered with a small amount of ethylacetate. Standing gives a crystalline solid which is filtered and washed with EtOAc and ether. Drying in vacuo gives 1.2 g (45%) of the dicyclohexyl amine salt as the hemihydrate, m.p. 108°–112° C.

(B) (±)-4-[[[[2-(Mercaptomethyl)-4-methyl-1-oxopentyl]amino]acetyl]amino]butanoic acid A solution of 0.7 g of (±)-4-[[[[2-[(acetylthio)methyl]-4-methyl-1-oxopentyl]amino]acetyl]amino]-butanoic acid, N-cyclohexylcyclohexanamine salt (1:1) in 25 ml of water is covered with ether and blanketed with argon. A solution of NaOH (10%) in water (3 ml) is added. After ½ hour, the aqueous is separated, acidified (10% KHSO$_4$) and extracted with ethyl acetate. Drying (Na$_2$SO$_4$) and evaporation gives an oil. Drying in vacuo over P$_2$O$_5$ gives the title compound as a viscous oil.

EXAMPLE 62

(±)-N$^2$-[N-[2-(Mercaptomethyl)-4-methyl-1-oxopentyl]glycyl]-L-argininamide, monoacetate salt A. (±)-N$^2$-[N-[2-[(Acetylthio)methyl]-4-methyl-1-oxopentyl]glycyl]-L-argininamide, monoacetate salt A solution of 0.76 g (2 mmoles) of N-[2-[(acetylthio)methyl]-4-methyl-1-oxopentyl]glycine, p-nitrophenyl ester (as prepared in U.S. Pat. No. 4,235,885) in 20 ml of dry THF at 0° C. is treated with a solution of 0.26 g (1 mmole) of argininamide diacetate salt in 5 ml of water, followed by 0.1 g (1 mmole) of triethylamine. The yellow solution is stirred at 0°–25° for 2 days, then evaporated to an aqueous solution and extracted with ethyl acetate until colorless. The aqueous is lyophilized, and the resulting powder stirred for several hours with acetonitrile. Filtration and drying in vacuo over P$_2$O$_5$ gives 0.4 g (80%) of a beige solid, m.p. 90°–110°, which analyzed for the presence of 1.25 moles of water of hydration, and 1 mole of acetic acid.

B. (±)-N$^2$-[N-[2-(Mercaptomethyl)-4-methyl-1-oxopentyl]glycyl]-L-argininamide, monoacetate salt An 0.2 g (0.4 mmole) sample of (±)-N$^2$-[N-[2-[(acetylthio)methyl]-4-methyl-1-oxopentyl]glycyl]-L-argininamide, monoacetate salt in 5 ml of water under argon at 0° is treated with 1 ml of concentrated NH$_4$OH. The mixture is stirred at 0°–25° for 3 hours, then lyophilized to give a gum which is stirred under argon with acetonitrile until a free flowing solid is formed; the solid is filtered and dried in vacuo over P$_2$O$_5$ at 25° to give the title compound in the form of 0.15 g (83%) of beige solid, m.p. 110°–120°.

EXAMPLE 63

N$^2$-[N-[N-[2-(Mercaptomethyl)-4-methyl-1-oxopentyl]-glycyl]glycyl]-L-arginine

N-(2-(S-acetylmercaptomethyl)-4-methyl-1-oxopentyl glycine prepared as described in Example 59A above and in U.S. Pat. No. 4,235,885 (6.1 g, 0.024 mole) is dissolved in 150 ml dioxane. This solution is cooled to 15° C. and N-hydroxysuccinimide (2.7 g, 0.024 mole) is added, followed by the portionwise addition of dicyclohexylcarbodiimide. This is stirred at room temperature overnight. Dicyclohexylurea is filtered off and the filtrate is concentrated in vacuo. Ethyl acetate (150 ml) is added to the residue and placed in the freezer for 1.5 hours. Additional dicyclohexylurea is filtered off and the filtrate again concentrated in vacuo. The product crystallizes and is washed with isopropyl ether to yield 7.8 g of the N-hydroxysuccinimide ester of N-(2-(S-acetylmercaptomethyl)-4-methyl-1-oxopentylglycine m.p. 82°–89° C.

Glycine (1.63 g, 0.022 mole) is dissolved in 20 ml of water containing NaHCO₃ (1.82 g, 0.022 mole). This is added dropwise to a solution of the above active ester (7.8 g, 0.022 mole) in 100 ml of DMF. After stirring overnight the solution is concentrated in vacuo. The residue is dissolved in 100 ml of water. This is acidified with 10% aqueous HCl at 0° C. and product is extracted with ethyl acetate. The ethyl acetate solution is dried with MgSO₄, filtered and concentrated in vacuo to yield 8.2 g of N-[N-[2-(mercaptomethyl)-4-methyl-1-oxopentyl]glycyl]glycine as an oil which is purified by preparing the dicyclohexylamine salt in ethyl acetate, m.p. 152°–156° C.

The free acid is liberated from the dicyclohexylamine salt by dissolving in water and acidifying with 10% aqueous KHSO₄. The product is extracted with ethyl acetate. The ethyl acetate solution is dried with MgSO₄, filtered and concentrated to 5 ml. This is poured on top of a 50 g pad of silica and filtered through with ethyl acetate. The ethyl acetate is concentrated in vacuo to yield 3.8 g of N-[N-[2-(mercaptomethyl)-4-methyl-1-oxopentyl]glycyl]glycine as an oil.

The above product (0.75 g, 0.0024 mole) is dissolved in 50 ml ethyl acetate. This is cooled to −5° C. and p-nitrophenol is added followed by the portionwise addition of dicyclohexylcarbodiimide. The reaction mixture is stirred at −5° C. for 2 hours. The formed dicyclohexylurea is filtered off. After concentrating to a 10 ml volume, the reaction mixture is cooled overnight. More dicyclohexylurea is formed. This is filtered and the filtrate is concentrated in vacuo to yield 0.95 g of active ester, (the p-nitrophenyl ester of N-[N-[2-(mercaptomethyl)-4-methyl-1-oxopentyl]glycyl]glycine).

The above crude active ester (0.95 g) is dissolved in 50 ml of THF. A solution of arginine (0.30 g) in 10 ml of water is added all at once to the THF solution at −5° C. The reaction mixture is stirred at room temperature overnight and concentrated in vacuo. The residue is dissolved in 25 ml of water and this solution is washed with ethyl acetate until the aqueous solution is almost colorless. The aqueous solution is lyophilized overnight to yield 0.65 g of analytical product N²-[N-[N-[2-(acetylmercaptomethyl)-4-methyl-1-oxopentyl]glycyl]glycyl]-L-arginine, m.p. 120°–130° C.

The above S-acetyl compound is dissolved in 15 ml of water which has previously been purged with argon. To this is added 0.8 ml of 37% NH₄OH and this solution is stirred for 2.5 hours under argon. It is lyophilized overnight, then suspended in acetonitrile and stirred under argon for 2.0 hours. Product is filtered and dried in vacuo for 4 hours to yield 0.44 g N²-[N-[N-[2-(mercaptomethyl)-4-methyl-1-oxopentyl]glycyl]glycyl]-L-arginine.

EXAMPLE 64

N²-[N-[N-[2-(Mercaptomethyl)-4-methyl-1-oxopentyl]glycyl]glycyl]-L-leucyl]-L-arginine The S-acetyl-(2-(mercaptomethyl)-4-methyl-1-oxopentyl)glycyl glycine prepared as described in Example 63 (1.0 g) is dissolved in dioxane. To this is added (0.36 g) of N-hydroxysuccinimide followed by the portionwise addition of DCC. The reaction mixture is stirred at ambient temperature overnight. The dicyclohexyl urea is filtered off and the filtrate is concentrated in vacuo. It is dissolved in ethyl acetate, washed with water, dried with MgSO₄, filtered and concentrated in vacuo to yield 1.0 g of active ester. The active ester is dissolved in 40 ml of DMF. This is cooled to 0° C. and an aqueous solution of NaHCO₃ (0.2 g) and leucine (0.32 g) is added to the DMF. After stirring at room temperature overnight, the reaction is concentrated in vacuo. To the residue is added 150 ml of water and the aqueous solution is washed with ethyl acetate. It is then acidified with 10% HCl and product is extracted with ethyl acetate. The ethyl acetate is dried with MgSO₄, filtered and concentrated in vacuo to yield 1.0 g of N-[N-[N-[2-(acetylmercaptomethyl)-4-methyl-1-oxopentyl]glycyl]glycyl]-L-leucine.

The above material (0.9 g) is dissolved in dioxane and cooled to 15° C. N-hydroxysuccinimide (0.23 g) is added followed by the portionwise addition of dicyclohexylcarbodiimide (0.4 g). After stirring at room temperature overnight, the reaction mixture is filtered and concentrated in vacuo. The crude is dissolved in ethyl acetate and washed with water. The ethyl acetate is dried with MgSO₄, filtered and concentrated in vacuo. NMR consistent with desired product; yield 0.9 g of the N-hydroxysuccinimide ester of N-[N-[N-[2-(acetylmercaptomethyl)-4-methyl-1-oxopentyl]glycyl]glycyl]-L-leucine. On standing, product crystallizes to yield low melting 38°–40° C. solid.

The above active ester (0.8 g) is dissolved in 40 ml of DMF. Arginine (0.2 g) is dissolved in 10 ml of water and added to the DMF solution. After stirring overnight, it is concentrated in vacuo to a viscous oil. This oil is triturated with acetonitrile under argon for 1 hour to yield N²-[N-[N-[N-[2-(acetylmercaptomethyl)-4-methyl-1-oxopentyl]glycyl]glycyl]-L-leucyl]-L-arginine (0.65 g).

The above sample is dissolved in 15 ml H₂O and 10 ml of methanol. The solution is cooled to 5° C. and purged with argon followed by the addition of 3 ml of concentrated ammonium hydroxide. The solution is stirred for 2 hours and lyophilized overnight. The sample is dried in vacuo over P₂O₅ to yield N²-[N-[N-[N-[2-(mercaptomethyl)-4-methyl-1-oxopentyl]glycyl]glycyl]-L-leucyl]-L-arginine.

What is claimed is:

1. A compound of the formula

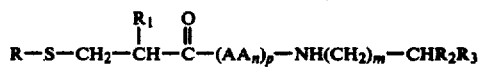

or salts thereof
wherein
R is hydrogen, alkanoyl of 2 to 10 carbon atoms or arylcarbonyl;
R₁ is alkyl of 3 to 8 carbon atoms, cycloalkyl of 3 to 7 carbon atoms, aryl or arylalkyl;
R₂ is hydrogen or

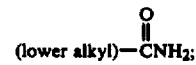

R₃ is

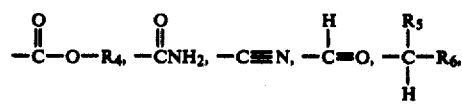

-continued

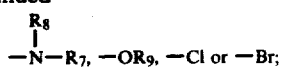

$R_4$ is hydrogen, lower alkyl or arylalkyl;

$R_5$ and $R_6$ are each independently selected as —OCH$_3$ or —OCH$_2$CH$_3$ or are combined as —OCH$_2$—CH$_2$—O— or —O—(CH$_2$)$_3$—O—;

$R_7$ and $R_8$ are each independently selected as hydrogen, lower alkyl or are combined as —(CH$_2$)$_4$—, —(CH$_2$)$_5$— or —CH$_2$CH$_2$—O—CH$_2$CH$_2$—;

$R_9$ is hydrogen, lower alkyl,

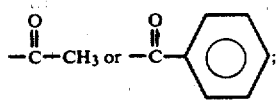

m is an integer from 0 to 7; p is an integer from 1 to 3 with the proviso that when p is 1, $R_2$ is -(lower alkyl)

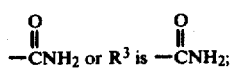

$AA_n$ is an amino acid chain or from one to three amino acids; n is 1 or 1, 2 or 1, 2, 3;

when p is 1, $AA_n$ is $AA_1$;

when p is 2, $AA_n$ is $AA_1$—$AA_2$;

when p is 3, $AA_n$ is $AA_1$—$AA_2$—$AA_3$;

$AA_1$ is glycine or alanine;

$AA_2$ is glycine or alanine;

$AA_3$ is leucine, glutamine or isoleucine, and physiologically acceptable salts thereof.

2. A compound of claim 1 wherein R is hydrogen, $R_3$ is

and m is 0 to 3.

3. A compound of claim 2 wherein n is 3.

4. A compound of claim 3 having the name N-[N-[[N-[2-(mercaptomethyl)-4-methyl-1-oxopentyl]-L-alanyl]-glycyl]-L-leucyl]-L-arginine.

5. The compound of claim 1 having the name ($\pm$)-$N^2$-[N-[2-(mercaptomethyl)-4-methyl-1-oxopentyl]glycyl]-L-argininamide, monoacetate salt.

6. The compound of claim 1 having the name $N^2$-[N-[N-[2-(mercaptomethyl)-4-methyl-1-oxopentyl]glycyl]-glycyl]-L-arginine.

7. The compound of claim 1 having the name $N^2$-[N-[N-[N-[2-(mercaptomethyl)-4-methyl-1-oxopentyl]-glycyl]glycyl]-L-leucyl]-L-arginine.

8. A pharmaceutical composition for reducing the adverse effects of mammalian collagenase which comprises a compound as defined in claim 1 and a pharmaceutically acceptable carrier therefor.

9. A method for reducing the adverse effects of mammalian collagenase in a mammalian host in need thereof, which comprises administering to said mammal an effective amount of a compound as defined in claim 1.

10. A method for treating rheumatoid arthritis in a mammalian host, which comprises administering an effective amount of a compound as defined in claim 1.

* * * * *